United States Patent [19]

Kaufhold et al.

[11] Patent Number: 5,371,270

[45] Date of Patent: Dec. 6, 1994

[54] METHOD OF MANUFACTURING CHLORINE-FREE CYCLOPROPANECARBOXYLIC ACID METHYL ESTER

[75] Inventors: Manfred Kaufhold; Josef Metz, both of Marl, Germany

[73] Assignee: Huels Aktiengesellschaft, Marl, Germany

[21] Appl. No.: 59,319

[22] Filed: May 11, 1993

[30] Foreign Application Priority Data

Jul. 9, 1992 [DE] Germany .............................. 4222497

[51] Int. Cl.⁵ .............................................. C07C 69/74
[52] U.S. Cl. ...................................... 560/124; 568/700
[58] Field of Search ........................ 560/124; 568/700

[56] References Cited

U.S. PATENT DOCUMENTS

| | | | |
|---|---|---|---|
| 2,992,269 | 7/1961 | Horrom | 560/124 |
| 3,077,496 | 2/1963 | Julia | 560/124 |
| 3,123,629 | 3/1964 | Julia | 560/124 |
| 3,294,833 | 12/1966 | Phillips | 560/124 |
| 3,711,549 | 1/1973 | Phillips | 560/124 |
| 4,520,209 | 5/1985 | Schwarze | 560/124 |
| 4,590,292 | 5/1986 | Blackwell | 560/124 |
| 4,778,920 | 10/1988 | Kaufhold | 560/124 |

FOREIGN PATENT DOCUMENTS

| | | |
|---|---|---|
| 1939759 | 3/1970 | Germany . |
| 2008110 | 5/1979 | United Kingdom . |

*Primary Examiner*—Michael L. Shippen
*Attorney, Agent, or Firm*—Oblon, Spivak, McClelland, Maier, & Neustadt

[57] ABSTRACT

A method of manufacturing chlorine-free cyclopropanecarboxylic acid methyl ester is described wherein a first portion of alkali methoxide is added to a high-boiling solvent, followed by a second portion of methoxide with an equimolar portion of 4-chlorobutyric acid. The ester product can be readily hydrogenated catalytically to the corresponding carbinol.

20 Claims, No Drawings

METHOD OF MANUFACTURING CHLORINE-FREE CYCLOPROPANECARBOXYLIC ACID METHYL ESTER

BACKGROUND OF THE INVENTION

Field Of the Invention

The invention relates to a method of manufacturing pure, chlorine-free cyclopropanecarboxylic acid methyl ester by the following reaction (I):

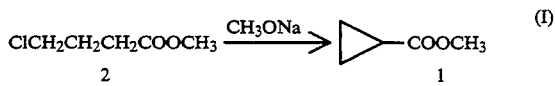

4-chlorobutyric acid methyl ester 2 is reacted with sodium methoxide in a high boiling solvent at 100°-200° C. with simultaneous distilling-off of the resulting cyclopropanecarboxylic acid methyl ester 1. The ester 1 is then purified by fractional distillation, and may be catalytically hydrogenated to the carbinol.

DISCUSSION OF THE BACKGROUND

Cyclopropanecarboxylic acid methyl ester 1 is an important raw material for the pharmaceutical industry. There are many examples of its synthesis by the reaction of 4-chlorobutyric acid methyl ester with strongly basic substances. For instance, U.S. Pat. No. 3,294,833, suggests sodium amide as the basic substance, while Ger. AS 19 39 759 and Ger. OS 27 51 133 both recommend sodium methoxide in toluene.

In carrying out these methods, the basic substance is mixed with an inert solvent, the mixture is heated, and the 4-chlorobutyric acid methyl ester is added. A complication arises because the methanol which forms must be distilled off in an azeotrope. Otherwise, the low boiling point of the methanol will result in a lowering of the reaction temperature, thereby extending the reaction time. Further, when sodium amide is used, an ammonia gas stream is generated which must be disposed of.

These methods also employ suspensions, which tend to cause gumming and adhesion of thermally generated residues to equipment surfaces, and thus are invariably accompanied by numerous technical problems. For instance, if solid alkoxide precipitates in the apparatus, under the high temperature conditions there is a hazard of explosion. Accordingly, these processes must be carried out at high dilution, which is detrimental to the space-time yield.

In an attempt to overcome these problems, Ger. Pat. 2,941,211 suggests a solvent comprising a solution of sodium methoxide in methanol. The reaction temperature is either high (e.g. 155°-160° C.) and carried out under pressure, or a more moderate temperature is used (e.g. 90°-100° C.) but the reaction is carried out under highly regulated conditions. In the latter case, either a precise amount of methanol must be distilled off, or a specially designed reaction evaporator must be used which likewise requires precision control. The further refinement of the reaction products is costly and isolation of the final product requires an extraction with dichloromethane. This last step leads to waste waters contaminated with methanol, creating costly disposal problems.

A more serious drawback of the method of Ger. Pat 2,941,211 is the low purity of the cyclopropanecarboxylic acid esters obtained. The chlorine content of these esters is high, generally 100-1,000 ppm or higher, as a result of which they cannot be catalytically hydrogenated to cyclopropylcarbinol. When catalytic hydrogenation is attempted, corrosion occurs in the reactor, and the hydrogenation catalyst is poisoned. Esters intended to be subjected to catalytic hydrogenation must be chlorine free, i.e. have a chlorine content $<10$ ppm (by weight, calculated as $Cl^-$). The only reagents which are candidates for reducing these high chlorine-containing cyclopropanecarboxylic acid esters are costly, e.g. lithium aluminum hydride.

Eur. OS 0,220,412 describes a method of manufacturing pure, chlorine-free (i.e., chlorine content $<10$ ppm) cyclopropanecarboxylic acid esters which are suitable as feedstocks for catalytic hydrogenation- A disadvantage of this method is that one first produces the butyl ester which then must be transesterified in a subsequent reaction step with a higher boiling alcohol having more than 4 carbon atoms. When the butyl ester was fed to hydrogenation, the product mixture obtained can be purified only by costly distillation.

All of the known methods thus require costly chemicals and pressure apparatus, lead to problems of waste disposal, require additional synthesis steps, and/or provide inadequate space-time yields. Therefore it is desirable to have a method wherein 4-chlorobutyric acid methyl ester is reacted with sodium methoxide in an ordinary stirred apparatus without pressurization and without special control means, and wherein the product comprises chlorine-free cyclopropanecarboxylic acid methyl ester.

Surprisingly, this problem is solved by a method whereby chlorine-free cyclopropanecarboxylic acid methyl ester is produced from 4-chlorobutyric acid methyl ester by the proper selection of reaction conditions. The cyclopropanecarboxylic acid methyl ester produced may be used, e.g., in catalytic hydrogenation to form cyclopropylcarbinol.

The use of the methyl ester as a starting material for the hydrogenation has a basic advantage over the esters produced according to Eur. OS 0,220,412, namely that cyclopropylcarbinol can be produced with a substantial higher space-time yield. This is because the reaction space required by $C_4$ and higher alcohols according to Eur. OS 0,220,412 (which alcohols are produced in the molar equivalent amounts) is much greater than that required by methanol.

SUMMARY OF THE INVENTION

Accordingly, one object of this invention is to provide a method whereby one can produce a cyclopropanecarboxylic acid ester from a 4-chlorobutyric acid ester with excellent space-time yields using no special chemicals or apparatus and having no waste disposal problems.

Another object is to provide a method of producing an essentially chlorine-free ($<10$ ppm) acid ester which can be catalytically hydrogenated to cyclopropylcarbinol.

A still further object is to allow the simple further processing of the reactor bottoms product, which comprises only high boiling solvent and sodium chloride. The sodium chloride can be removed by filtration or washing with water, and the solvent can be reused.

The present method of providing chlorine-free cyclopropanecarboxylic acid methyl ester comprises the following steps:

(a) a high boiling solvent is charged to the reactor and is heated, e.g. to 120°–130° C.;

(b) a first portion of alkali methoxide (e.g.: sodium methoxide) is added, under stirring, as a "starting amount", producing a readily stirrable thin liquid suspension;

(c) alkali methoxide and 4-chlorobutyric acid methyl ester are then added, simultaneously;

(d) the remaining 4-chlorobutyric acid methyl ester (if any) is added;

(e) during the process, the cyclopropanecarboxylic acid methyl ester is preferably distilled off continuously, along with methanol, as soon as it is produced;

(f) preferably, pure chlorine-free product is then obtained by fractionally distilling this methanol-ester mixture.

It is surprising that one only obtains the ester product in chlorine-free form and in good yields of >85% if one carries out the combination of all of the described steps (a–f, above). Prior to the purifying distillation the raw ester still has a high chlorine content of 100–500 ppm; i.e., the low chlorine content of the final product is not the result of a quantitative conversion. If one does not carry out the second step, for example, the chlorine content after purifying distillation will fluctuate widely from instance to instance. If instead, one employs a "starting amount" of the chlorobutyric acid ester, the purifying distillation will yield a chlorine-containing ester with an unsatisfactory chlorine content of 50–200 ppm.

DESCRIPTION OF THE PREFERRED EMBODIMENTS

A more complete appreciation of the invention and many of the attendant advantages thereof will be readily obtained as the same becomes better understood by reference to the following detailed description.

A stirred apparatus is employed which is not fitted with a distillation column but has a distillation bridge. A high boiling solvent is charged to the apparatus. The boiling point of the solvent should be at least >100° C., more preferably >150° C., even more preferably >250° C., and most preferably >280° C. The solvent must be inert to sodium methoxide, and thermally stable, but otherwise is not subject to any special limitations.

For reasons of economics, one would select an inexpensive hydrocarbon, e.g. an alkylaryl compound or a mixture of alkylaryl compounds, such as n-$C_{10}$-$C_{13}$-alkylbenzene, tetrapropylbenzene, etc.

The solvent is heated to 100°–200° C., preferably 100°–150° C., particularly preferably 120°–140° C., and is stirred. Then a first portion of the alkali methoxide to be used is added, in solid form or as a methanolic solution. By "first portion" is meant at least some, but not all, of the total amount of alkali methoxide used. If a methanolic solution is used, the methanol is subsequently distilled off. This first portion is preferably 5–50%, more preferably 10–30%, particularly preferably 20–25%, of the total amount alkali methoxide used.

Thereafter, a second portion of alkali methoxide and 4-chlorobutyric acid ester are added simultaneously. It is preferred that these be added in stoichiometric ratio (equimolar amounts), so that the "starting amount" of alkali methoxide is preserved. Preferably this addition occurs immediately after the addition of the "starting amount" of alkali methoxide. By "second portion" is preferably meant the remaining portion of alkali methoxide to be used. When the addition of the first and second portions of alkali methoxide has been completed, any remaining 4-chlorobutyric acid ester to be used is then added. It is preferred that after the simultaneous addition of alkali methoxide and 4-chlorobutyric acid ester, the only remaining addition, if any, is 4-chlorobutyric acid ester. During the entire period of addition of the 4-chlorobutyric acid ester, a mixture of methanol and cyclopropanecarboxylic acid methyl ester is, preferably, continuously distilled off.

At the conclusion of the reaction, a vacuum may be applied, and the remaining cyclopropanecarboxylic acid methyl ester is distilled out of the inert solvent.

The molar ratio of sodium methoxide to 4-chlorobutyric acid methyl ester used overall is preferably 1:1 to 2:1, more preferably 1:1 to 1.5:1, even more preferably 1.1:1 to 1.2:1.

The weight ratio of solvent to 4-chlorobutyric acid ester used is preferably 1:1 to 1:2, more preferably 1:1 to 1:1.5, even more preferably 1:1 to 1:1.1.

The resulting cyclopropanecarboxylic acid methyl ester may be used, e.g., for producing hydroxymethylcyclopropane (cyclopropylcarbinol) by hydrogenation. Cyclopropylcarbinol is an important intermediate product in the manufacture of pharmaceuticals. Preferably, the hydrogenation is carried out in the bottoms and trickling phase of a Zn chromite catalyst, at 200°–350° C. and a hydrogen pressure of 200–320 bar.

The aforementioned process may also be applied to the more general case wherein a haloalkyl acid ester is reacted with an alkali alkoxide to yield a cycloalkyl acid ester. However, acid esters containing a $\gamma$-halogen, wherein the halogen is chlorine or bromine are preferred. The alkoxide is preferably methoxy and the alkali metal counter ion is preferably sodium. The temperature ranges disclosed herein are for the previously mentioned reaction (I), above, but the optimum temperature to be used for, e.g., 4-bromobutyric acid methyl ester reacted with sodium methoxide can be readily determined by the skilled artisan with the present disclosure.

Having generally described this invention, a further understanding can be obtained by reference to certain specific examples which are provided herein for purposes of illustration only and are not intended to be limiting unless otherwise specified.

EXAMPLE 1

A glass apparatus was used, comprising a three-necked flask with a stirrer, a thermometer, and a 10 cm long Vigreux column with distillation bridge. This apparatus was connected to two dosing pumps which drew from feed vessels.

500 g of an n-$C_{10}$-$C_{13}$-alkylbenzene (trade name Marlican) was added, and was heated to 134° C.

Then 200 ml of a 30% sodium methoxide solution was added over a period of 0.5 hr, and the methanol was distilled off. Then doses of 80 ml of a 30% sodium methoxide solution simultaneously with 50 ml 4-chlorobutyric acid methyl ester were pumped in over a period of an additional 0.5 hr per dose, until 800 ml (corresponding to 810 g, 4.50 mol) sodium methoxide solution and 485 ml (=557 g, 4.07 mol) 4-chlorobutyric acid methyl ester had been added. During this period a mixture of methanol and ester was distilled off. The overhead temperature increased from 66° C. to 76° C., and then decreased to 66° C. as the end of the reaction was approached. After 5.5 hr the simultaneous addition of the methyl ester and methoxide was concluded. The mixture was then stirred at 130° C. for an additional 0.5 hr, followed by cooling to 80° C. In order to distill the residual cyclopropanecarboxylic acid methyl ester out of the bottoms, an underpressure of 100 mbar was applied. 123 g distillate was collected in a boiling range 33°–49° C.

Total amount of distillate collected = 1059 g.

Chlorine content = 300 ppm.

This raw product was fractionally distilled at normal pressure in a 0.5 m long column packed with Multifil packing. At 117° C., 359 g cyclopropanecarboxylic acid methyl ester was collected, having purity 99.9% and a chlorine content of only 3.5 ppm. The yield (based on the amount of reactants) was 88.0% of theoretical.

EXAMPLE 2 AND 3 (Comparative Examples)

The same apparatus, materials, and quantities were used as in Example 1, except that the sodium methoxide solution and the 4-chlorobutyric acid methyl ester were pumped simultaneously into the reactor (i.e. there was no "starting amount" of methoxide). The procedure was otherwise the same as described for Example 1. The cyclopropanecarboxylic acid methyl ester was obtained in a yield of 85.6% had chlorine content 190 ppm.

A repetition of this experiment yielded the cyclopropanecarboxylic acid methyl ester in a yield of 83.8%, with chlorine content 80 ppm. Thus, with this method, the chlorine content fluctuated widely and was too high.

EXAMPLE 4

The same apparatus, materials, and method were used as in Example 1, except that the reaction temperature selected was 110° C. instead of 130° C. The reactor contents accumulated during the procedure, because the amount of product which was distilled off was too small. After product refinement, the yield was 87.6% and the chlorine content in the product was 7 ppm.

EXAMPLE 5

The method was as described in Example 4, except that the reaction temperature was 140° C. At this temperature, there is appreciable foaming, with the risk that product foam will pass over with the distillate. After product refinement, the yield was 87.9% and the chlorine content was 10 ppm.

EXAMPLES 6 AND 7

The method was as described in Example 1, except that half of the sodium methoxide which was to be used was employed as a "starting amount". A stirrable liquid suspension resulted which was substantially more viscous than that of Example 1. The results were comparable to those of Example 1.

When only 5% of the sodium methoxide solution was used as a "starting amount", the suspension was very inviscid; again the results were comparable to those of Example 1.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process of making a cycloalkylcarboxylic acid alkyl ester comprising:
   adding an inert solvent to a reactor;
   heating the reactor;
   adding a first portion of an alkali alkoxide to the reactor; then
   adding a second portion of an alkoxide simultaneously with haloalkylcarboxylic acid alkyl ester to the reactor;
   recovering cycloalkylcarboxylic acid alkyl ester from the reactor by distillation.

2. A method of manufacturing cyclopropanecarboxylic acid methyl ester by reacting 4-chlorobutyric acid methyl ester with an alkali methoxide in an inert solvent comprising:
   adding the inert solvent to a reactor;
   heating the reactor to 100°–200° C.;
   adding a first portion of the alkali methoxide to the reactor; then
   adding a second portion of the alkali methoxide simultaneously with 4-chlorobutyric acid methyl ester to the reactor;
   distilling off a mixture of methanol and cyclopropanecarboxylic acid methyl ester;
   recovering cyclopropanecarboxylic acid methyl ester by fractional distillation of said mixture.

3. The method according to claim 2, wherein the reaction is carried out at 100°–150° C.

4. The method according to claim 2, wherein the reaction is carried out at 120°–140° C.

5. The method according to claim 2, wherein a high boiling inert solvent is used which has a boiling point above 150° C.

6. The method according to claim 2, wherein a high boiling inert solvent is used which has a boiling point above 250° C.

7. The method according to claim 2, wherein a high boiling inert solvent is used which has a boiling point above 280° C.

8. The method according to claim 2, wherein the first portion of alkali methoxide added is 5–50% of the total amount of alkali methoxide used.

9. The method according to claim 2, wherein the first portion of alkali methoxide added is 10–30% of the total amount of alkali methoxide used.

10. The method according to claim 2, wherein the first portion of alkali methoxide added is 20–25% of the total amount of alkali methoxide used.

11. The method according to claim 2, wherein a mixture of methanol and cyclopropanecarboxylic acid methyl ester is distilled off continuously during the reaction, and at the conclusion of the reaction a vacuum is applied and the remaining cyclopropanecarboxylic acid methyl ester is distilled out of the solvent.

12. The method according to claim 2, wherein the molar ratio of alkali methoxide to 4-chlorobutyric acid methyl ester is 1:1 to 2:1.

13. The method according to claim 2, wherein sodium methoxide is used as the alkali methoxide.

14. The method according to claim 2, wherein the mixture of methanol and cyclopropanecarboxylic acid methyl ester obtained is distilled off continuously.

15. The method according to claim 2, wherein after adding the second portion of the alkali methoxide, 4-chlorobutyric acid methyl ester is added.

16. The method according to claim 2, wherein the recovered cyclopropanecarboxylic acid methyl ester contains less than 10 ppm chlorine.

17. The method according to claim 16, wherein the weight ratio of solvent to 4-chlorobutyric acid ester used is 1:1 to 1:1.1.

18. The method according to claim 12, wherein the molar ratio of alkali methoxide to 4-chlorobutyric acid methyl ester is 1:1 to 1.5:1.

19. The method according to claim 18, wherein the molar ratio of alkali methoxide to 4-chlorobutyric acid methyl ester is 1.1:1 to 1.2:1.

20. A method of manufacturing cyclopropylcarbinol by reacting 4-chlorobutyric acid methyl ester with an alkaline methoxide in an inert solvent comprising:
   adding the inert solvent to a reactor;
   heating the reactor to 100°–200° C.;
   adding a first portion of the alkali methoxide to the reactor; then
   adding a second portion of the alkali methoxide simultaneously with 4-chlorobutyric acid methyl ester to the reactor;
   distilling off a mixture of methanol and cyclopropanecarboxylic acid methyl ester;
   recovering cyclopropanecarboxylic acid methyl ester by fractional distillation of said mixture; and
   catalytically hydrogenating the cyclopropanecarboxylic acid methyl ester so as to form cyclopropylcarbinol.

* * * * *